United States Patent [19]

Ciullo, Jerome V.

[11] Patent Number: 4,696,293
[45] Date of Patent: Sep. 29, 1987

[54] HINGED EXTERNAL FIXATOR

[76] Inventor: Ciullo, Jerome V., 5914 Nottingham, Detroit, Mich. 48224

[21] Appl. No.: 432,090

[22] Filed: Sep. 30, 1982

[51] Int. Cl.$^4$ .............................................. A61F 5/04
[52] U.S. Cl. .............................. 128/92 ZK; 128/92 Z; 128/92 ZW
[58] Field of Search ................. 128/92 A, 92 R, 92 G, 128/92 D, 88, 92 Z, 92 ZZ, 92 ZK, 92 XP; 3/26-28

[56] References Cited

U.S. PATENT DOCUMENTS

| 3,242,922 | 3/1966 | Thomas | 128/92 R |
|---|---|---|---|
| 4,185,623 | 1/1980 | Volkov et al. | 128/92 A |
| 4,312,336 | 1/1982 | Danieletto et al. | 128/92 A |
| 4,338,927 | 7/1982 | Volkov et al. | 128/92 A |
| 4,372,298 | 2/1983 | Lerman | 128/88 |
| 4,403,607 | 9/1983 | Woo et al. | 128/92 D |
| 4,488,542 | 12/1984 | Helland | 128/82 Z |
| 4,548,199 | 10/1985 | Agee | 128/92 A |

FOREIGN PATENT DOCUMENTS

| 0011258 | 5/1980 | European Pat. Off. | 128/92 A |
|---|---|---|---|
| 2435938 | 4/1980 | France | 128/92 A |
| 534231 | 2/1977 | U.S.S.R. | 128/92 A |
| 594974 | 4/1978 | U.S.S.R. | 128/92 A |
| 686730 | 9/1979 | U.S.S.R. | 128/92 A |

OTHER PUBLICATIONS

Banks et al., "The Salford Technique for Rx of Complicated Tibial Fx", Engr. in Med., vol. 9, No. 2, Apr. 1980, pp. 84-86.
Ma et al., "Fibial Lengthening App. w/Distractive Force Measurement System", J. Biomed Engr. 1980, vol. 2, Oct., pp. 265-271.

Primary Examiner—C. Fred Rosenbaum
Assistant Examiner—C. W. Shedd
Attorney, Agent, or Firm—Harness, Dickey & Pierce

[57] ABSTRACT

Traction across a joint of the body is provided by the hinged external fixator which holds bony parts by means of screws or pins embedded in the bony parts. The hinged external fixator permits portable traction allowing early mobilization, wound care, and flexing and exercise of the articular cartilage to promote healing and to prevent post traumatic arthritis. An adjustable distension apparatus, having an integral spring biased force garage, provides conveniently alterable and measurable traction forces.

12 Claims, 11 Drawing Figures

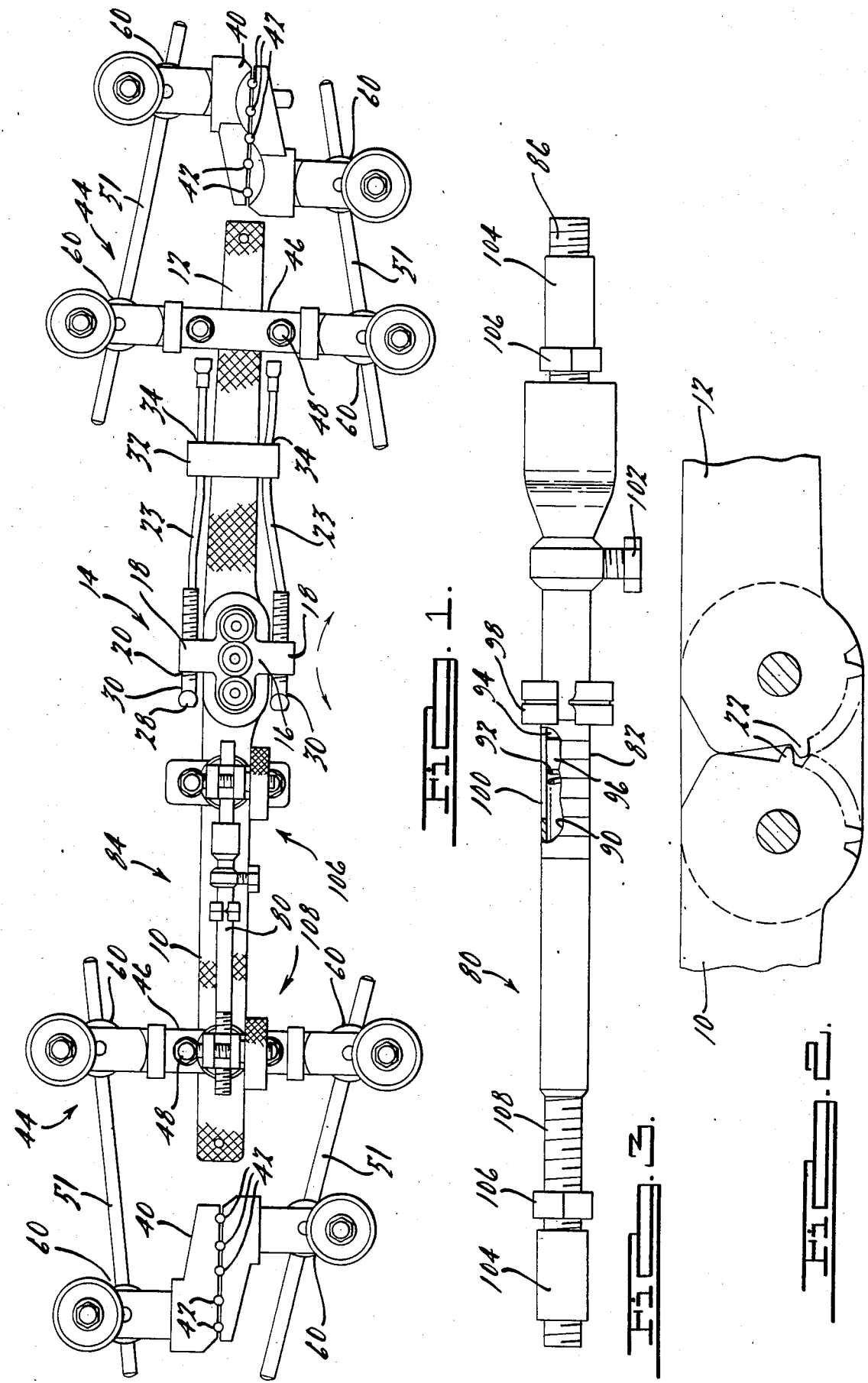

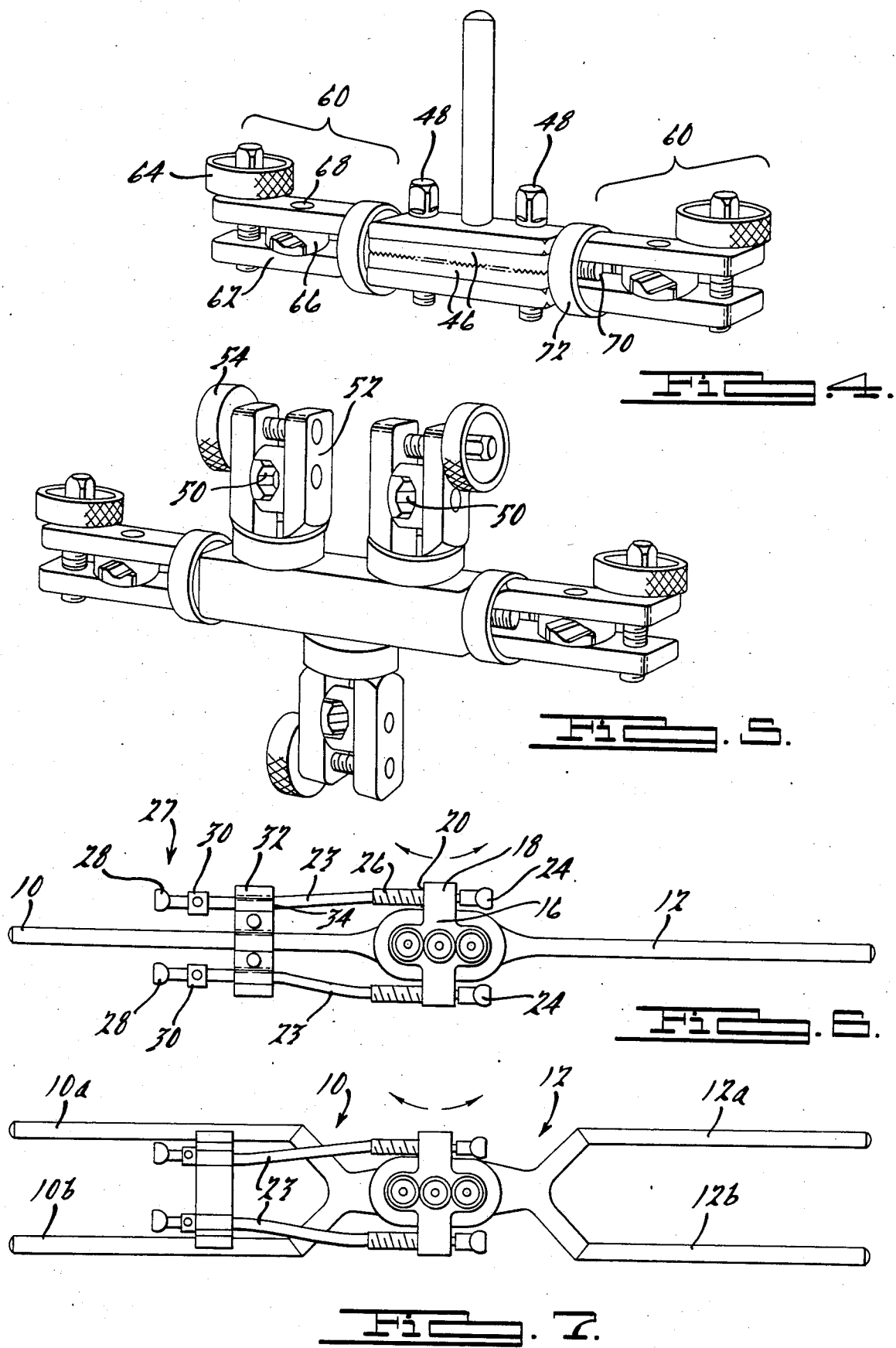

HINGED EXTERNAL FIXATOR

BACKGROUND OF THE INVENTION

The present invention relates generally to medical equipment and more particularly to an apparatus for applying traction to any of the major joints of the body. The apparatus of the present invention permits early motion and exercise of articular cartilage while maintaining distraction across the joint, thus reducing or eliminating post traumatic disorders such as arthritis, maintaining anotomic relations following surgical tissue repair of implantation, preventing tissue disruption, implant loosening or failure.

An external fixator can be used to hold two bones or bone fragments, such as for example, two pieces of a broken bone, in a fixed position relative to one another to facilitate the healing process. Generally speaking, pins are planted in the bone fragments and then the external fixator is secured to the pins to hold the pins, and the bone fragments attached thereto, in fixed position relative to each other.

In accordance with the present invention, an external fixation is provided which is well adapted to apply traction across a joint to allow reduction of intra-articular fractures by surrounding tissue pressure. Although this can be alternatively accomplished by use of traction conventionally provided by weights through the distal extremity at bed rest, this alternative has the disadvantage of not permitting the patient to move about so as to exercise the affected articular cartilage. Conventional external fixators are likewise not well adapted to permit exercise of the joint. Motion of a joint is useful in reducing or eliminating post traumatic disorders such as post traumatic arthritis which can be reduced or eliminated by proper exercise of cartilage. In short, by applying an external fixator of the present invention across a joint in a distraction mode, distension can be used to allow ligamentotaxis, i.e. tissue pressure reduction of the fracture.

The use of weights for applying traction through the distal extremities at bed rest has the disadvantage of not permitting the patient to move about so as to exercise the affected articular cartilage and conventional external fixators likewise not well adapted to permit exercise of the joint. Furthermore, when producing traction forces for tissue pressure reduction of the fracture, the magnitude of such forces should be adjustable and capable of ready measurement so that the proper traction can be applied to best suit the patient's needs.

Accordingly, the hinged external fixator of the present invention provides a portable traction device which can be applied to any of the major joints of the extremities, and selectively allow limited exercise of the joint which can be changed as therapy progresses. Post-traumatic or post-surgical stability of a joint is attained through such portable traction allowing early mobility and exercise even while aligning fracture fragments and injured tissues, or protecting surgical implants and/or tissue repairs. As will be further appreciated from the drawing and the disclosure which follows, the device of the present invention also provides readily adjustable traction or distraction forces and measurement thereof.

SUMMARY OF THE INVENTION

The present invention comprises an articulated external fixator for maintaining bony parts in position relative to one another to promote proper healing of bone and associated soft tissue. The device comprises first and second elongated structural members which are coupled to one another for articulated movement. The elongated structural members each have cooperating toothed end portions forming an articulated joint for transmitting articulated motion of one of the elongated members relative to the other member. An adjustable cable-type limiting means is disposed on one of the elongated structural members and serves to selectively limit the articulated movement of the joint. More specifically, the limiting means comprises a pair of cables which are adjustably secured to a linkage structure pivotally secured to and forming an integral part of the articulated joint or hinge. Each cable has a threaded end portion which may be selectively rotated within corresponding threaded bore on the linkage member so as to axially translate the cable and thereby lengthen or shorten the cable's effective length. The intermediate portion of each cable is slidably received by a bracket disposed on one of the elongated members and the opposite end of each cable is provided with a stop means or nut engagable with the bracket to limit the articulated movement of the elongated structural members.

At the outer end of each structural member is a clamp for holding one or more pins to be inserted into the bony parts. The holding clamps are secured directly to the respective ends of the elongated members, while one of the holding clamp is further attached to the end of an adjustable distension means or turnbuckle. The turnbuckle in turn is secured to an intermediate portion of the other of said elongated structural members. The turnbuckle includes a threaded shaft and internally threaded outer housing which cooperate to lengthen or shorten upon rotation of the shaft or housing. By rotating the turnbuckle shaft the holding clamp carried thereon can be displaced relative to the other holding clamp. The turnbuckle distension means also includes a spring loaded or biased force gauge for measuring the traction forces produced.

Other objects, features, and advantages of the present invention will become apparent from the subsequent description and the appended claims, takes in conjunction with the accompanying drawings, in which:

BRIEF DESCRIPTION OF THE DRAWINGS

FIG. 1 is a top plan view of the invention;

FIG. 2 is a cross sectional view taken through the articulated joint or hinge;

FIG. 3 is an enlarged detail view of the turnbuckle distension member with integral force gauge;

FIGS. 4 and 5 are enlarged detailed views illustrating alternative embodiments of clamping members of the invention;

FIGS. 6, 7 and 8 are enlarged detailed views showing differnet embodiments of the articulated structural members of the invention;

DESCRIPTION OF THE PREFERRED EMBODIMENT

Figure 8:
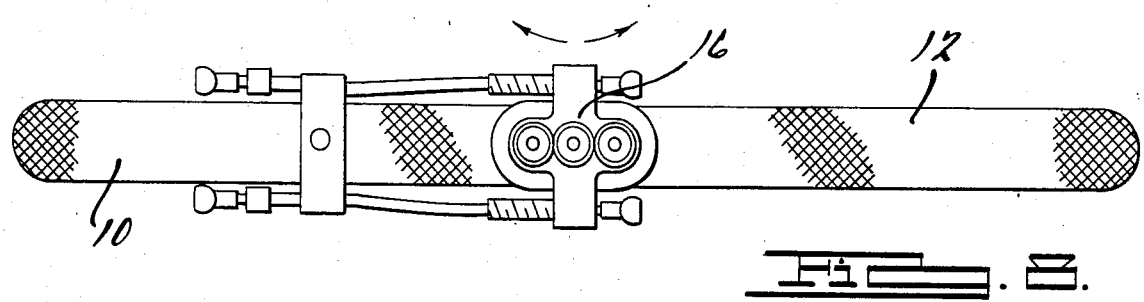

A first preferred embodiment of the invention is illustrated in FIG. 1 through 3, and 8. As illustrated, the invention comprises first and second elongated structural members 10 and 12 which are pivotally connected as at 14 for articulated movement. Structural member 10 and 12 may be, for example, steel bars having an inscribed cross-hatched outer surface so that clamps may be attached without slipping. The hinged joint or coupling 14 more specifically comprises a link member 16 to which structural members 10 and 12 are journaled for pivotal movement at their respective innermost ends. The coupling link 16 also includes a pair of outwardly projecting ears 18, each having a longitudinal threaded bore 20. With reference to FIG. 2 the innermost ends of structural members 10 and 12 are formed with cooperative intermeshing toothed or geared portions 22. The geared end portions 22 coact so that pivotal movement of one of the elongated structural members causes pivotal movement of the other elongated structural member in the opposite direction. Those skilled in the art will appreciate that this coaction gives the hinged joint a smooth positive action. Generally, however, other equivalent hinge mechanisms may be substituted therefor with good results.

It will further be recognized that the elongated structural members 10 and 12 need not be limited to the metal bar structure illustrated in FIG. 1 and 8. In this regard, FIGS 6 and 7 illustrate other structurally equivalent embodiments of the elongated structural members.

The elongated structural members 10 and 12 of FIG. 6 comprises elongated cylindrical rods, while members 10 and 12 of FIG. 7 comprise forked or bifurcated rods having generally parallel tines 10a and 10b and 12a and 12b respectively. FIG. 8 illustrates the elongated structural members 10 and 12 of the embodiment illustrated in FIG. 1.

With continued reference to FIGS. 6, 7 and 8, the invention further comprises an adjustable means for selectively limiting the articulated movement of the elongated structural members. In the presently preferred embodiment this adjustable limiting means comprises a pair of relatively flexible ropes or cables 23 which are adjustably secured at a first end thereof to link 16. More specifically, each cable is terminated in an end-cap 24 and is carried within an externally threaded tube 26. Threaded tube 26 is in turn threadedly secured within bore 20 for axial rotation. Threaded tube 26 engages with end-cap 24 so that rotation of tube 26 causes translation of cable 23. Such rotation has the effect of lengthening or shortening the operative portion of cable 23 as measured between ear 18 and the distal end 27 of the cable. The distal end 27 is provided with an end-cap 28 and stop nut 30. The mid-section of cable 23 is slidably carried in a bracket 32 secured to elongated structural member 10. Bracket 32 is provided with a pair of guide channels 34 for slidably receiving cables 23.

In use each of the cables 23 may be independently adjusted by rotating the corresponding threaded tube 26 to thereby lengthen or shorten the effective length of each cable. Articulated movement of the elongated structural members is checked when nut 30 comes to bear against bracket 32 as cable 23 slides within guide channel 34 upon rotation of the joint. It will be seen that by providing independently adjustable cables, secured on ears 18 on generally opposite sides of the articulated joint, the stop or limit to clockwise, i.e. flexion, and counter clockwise, i.e. extension, articulation can be independently controlled. Those skilled in the art will appreciate that this independent control is quite advantageous in some applications, particularly in limiting flexion and extension according to therapeutic plans.

With renewed reference to FIG. 1, the invention further comprises a pair of holding clamps 40 adapted to receive pins 42 to be inserted in the bony parts in the conventional fashion. Holding clamps 40 are disposed generally outwardly from the respective outermost ends of members 10 and 12 held in place by means of adjustable clamp-on brackets 44. It will be understood that the specific construction of clamp-on brackets 44 will vary depending on the particular configuration of the elongated structural members. For instance, if elongated members 10 and 12 take the form of a flat metal bar illustrated in FIG. 1, brackets 44 preferably includes coacting jaws 46 held in clamping engagement as with bolts 48. If the elongated structural members take the form of single or bifurcated rods, as shown generally in FIGS. 6 and 7, brackets 44 preferably includes a chuck fixture 50 for receiving and griping the structural member under pressure supplied by vice 52 and thumb screw adjustment 54. It will be understood that the foregoing clamping structures are provided by way of example only and are not intended to limit the scope of the invention. For example, supports 10 and 12 can alternatively be directly attached to pins 42 by means of an adhesive such as methyl methacrylate or direct clamping as in FIG. 11.

Figure 10:
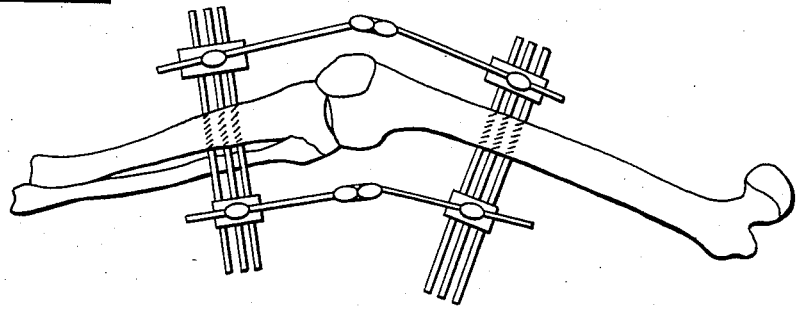
Figure 11:
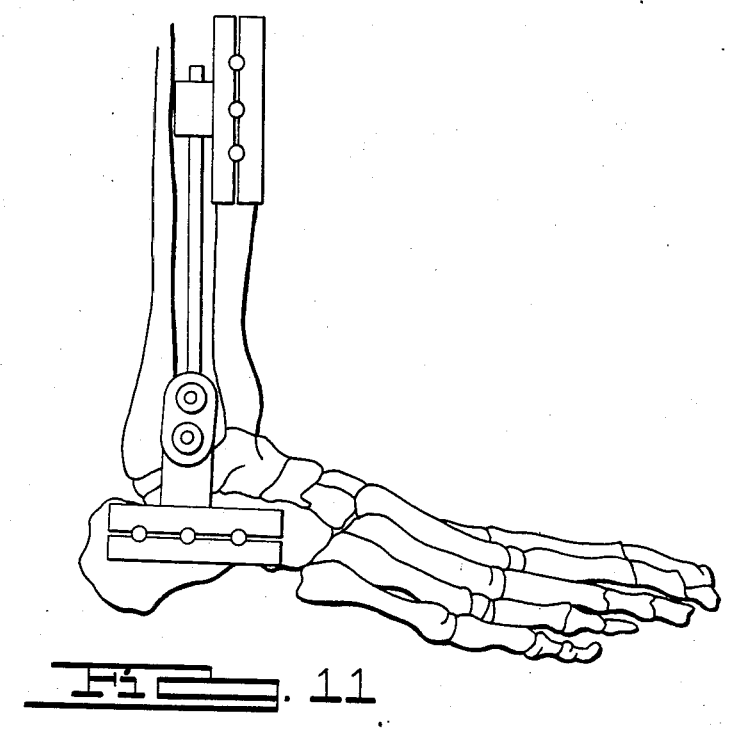

The holding clamps 40 are adjustably attached to the clamp-on brackets 44 by means of a pair of linkage rods 51 which may be secured with chuck and vice fixtures 60, generally of similar construction to chuck fixture 50 and vice 52. The chuck and vice fixtures 60 permit movement with multiple degrees of freedom as will be seen with reference to FIG. 4. While FIG. 4 specifically illustrates one particular clamp structure 44, the chuck and vice assembly 60 is essentially the same for any clamp structure embodiment. The chuck and vice fixture includes a vice 62 for providing clamping pressure by means of thumb screw 64 through engaging grooved chuck member 66. Chuck member 66 is pivotally secured as at 68 between the jaws of vice 62 thus permitting a member such as linkage rod 51 to slide and pivot in the plain of the vice when thumb screw 64 is loosened. Vice 62 is in turn carried for rotational movement on a threaded stud 70 which permits the plain of the vice to be rotated to any desired attitude. A threaded collar 72 is provided to check or lock the vice in a desired attitude by back tightening against the vice 62. Chuck and vice fixture 60 thus provides multiple degrees of freedom permitting the invention to be adapted for use with any of the joints of the body. In this regard, FIGS. 9, 10 and 11 illustrate a few of these uses.

The invention further includes an adjustable tension calibrating and distension device 80 having an integral gauge 82 for measuring traction forces. Referring to FIG. 3, the adjustable distension device generally comprises a shaft 86 and an outer housing 88 which telescopically cooperates with the shaft to lengthen or shorten the effective length of the distension device 80. Housing 88 has an internal axial recess 90 in which a calibration spring 92 is disposed. When shaft 86 is telescopically depressed into housing 88, the inserted end of 94 of the shaft 86 applies compression forces to calibration spring 92 acting through a nylon plug 96 disposed in recess 90 between the spring and end 94. A cursor 98 carried on nylon plug 96 slides in a longitudinal track 100 extending through the housing 88 to provide and indication of the forces being applied between housing 88 and threaded insert 86. The housing 88 may be provided with force gauge markings, scribed along the longitudinal slot or track 100 to provide force measurements in any convenient units of measure. Once the proper force is set, a set screw 102 may be engaged to lock the distension device. In the alternative, tension may be supplied by applying tension on the extremity, as with external weights or springs, using the force gauge to measure the tension, and then locking or tightening the brackets 44 securely to the elongated members. In order to provide a convenient means for attaching the distension device at its respective ends to the elongated structural member 10, both ends of the turnbuckle are provided with threaded collars 104 which may be locked in place by back tightening complimentary locking nuts 106. To accomodate the threaded collar, housing 88 and shaft 86 are provided with threaded end portions 108. The threaded collars 104 are in turn clamped as at 106 and 108 to the elongated structural member 10 using chuck and vice fixtures as were generally described above.

Alternatively, the shaft 86 and housing 88 may be threaded to act in the nature of a turnbuckle 84. In such an embodiment shaft 86 and housing 88 rotate cooperatively to shorten or lengthen the effective length of the distension device thereby generating tension or compression forces.

Figure 9:
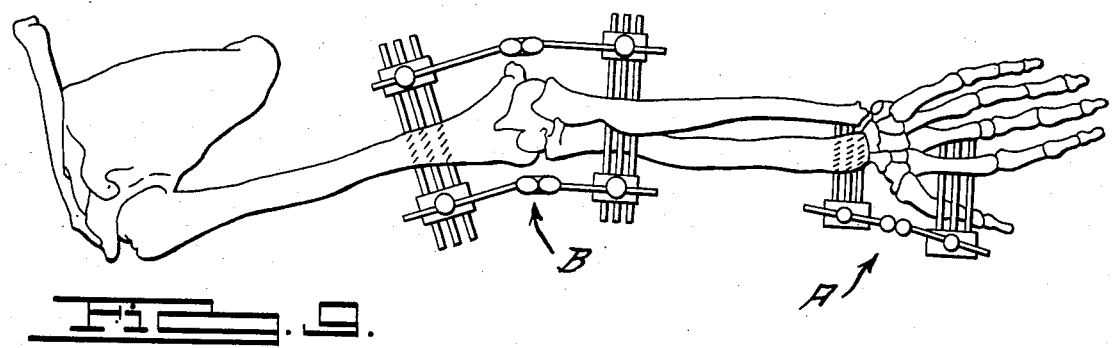
FIGS 9, 10 and 11 are abbreviated, schematic views illustrating several of the possible use configurations of the invention.

In use, the invention may be used either singly or multiply as illustrated in FIG. 9. In FIG. 9, single use is illustrated as at A and multiple use as at B. By adjusting the relative position of individual holding clamps, the invention may be used with many different types of fractures. FIGS. 9, 10 and 11 exemplify such uses.

While it will be apparent that the preferred embodiments of the invention disclosed are well calculated to fulfill the objects above stated, it will be appreciated that the invention is susceptible to modification, variation and change without the parting from the proper scope or fair meaning of the invention.

What is claimed is:

1. An articulated external fixator for the joint of at least a pair of articulated tubular bony parts, comprising: first and second elongated structural members having adjacent ends pivotally connected for generally only single axis pivotal movement with respect to one another about the anatomic axis of articulation of said bony parts, each of said first and second structural members adapted to be positioned on one or the other of said bony parts in distraction with longitudinal axis generally parallel to the longitudinal axis of the associated bony part so that said articulated movement of said structural members corresponds with the articulated movement of said bony parts about the joint;

first and second holding means carried on said first and second structural members respectively and adapted to receive pins to be inserted in the bony part; and limiting means for limiting the articulated movement of said structural members.

2. The apparatus of claim 1 wherein said limiting means is adjustable limiting means.

3. The apparatus of claim 2 wherein said adjustable limiting means comprises means for independently adjustably limiting clockwise and counter clockwise articulated movement of one of said elongated structural members.

4. The apparatus of claim 2 further comprising link means for pivotally securing said first and second elongated structural members and bracket means disposed on one of said elongated structural members, said adjustable limiting means comprising cable means adjustably secured at a first end thereof to said link means and slidably received by said bracket means, said cable means including stop means engagable with said bracket means to limit the articulated movement of said structural members.

5. The apparatus of claim 1 further comprising adjustable distension means carried on said first elongated structural member and coupled to said first holding means for producing traction forces in said bony parts, said distension means including gauge means for measuring said traction forces.

6. The apparatus of claim 5 wherein said distension means comprises turnbuckle means.

7. The apparatus of claim 6 wherein said turnbuckle means is adjustably clamped to said first elongated structural member.

8. The apparatus of claim 6 wherein said first holding means is adjustably clamped to said turnbuckle means.

9. The apparatus of claim 1 wherein said second holding means is adjustably clamped to said second elongated structural member.

10. The apparatus of claim 1 wherein said first and second elongated structural members have toothed joint means for transmitting articulated motion of one of said elongated structural members to the other of said elongated structural members.

11. A method of fixing two articulated tubular bony parts in proper relative position across a joint, comprising applying an articulated external fixator to each of said bony parts in distraction across said joint, said fixator having a single axis of articulation about the axis of articulation of said bony parts.

12. An articulated external fixator for the joint of at least a pair of articulated tubular bony parts, comprising: first and second elongated structrural members having adjacent ends pivotally connected for generally only single axis pivotal movement with respect to one another about the anatomic axis of articulation of said bony parts, each of said first and second structural members adapted to be positioned on one or the other of said bony parts in distraction with longitudinal axis generally parallel to the longitudinal axis of the associated bony part so that said articulated movement of said structural members corresponds with the articulated movement of said bony parts about the joint; and first and second holding means carried on said first and second structural members respectively and adapted to receive pins to be inserted in the bony parts.

* * * * *